United States Patent [19]

Spronken

[11] 4,425,721
[45] Jan. 17, 1984

[54] WALKING SOLE

[75] Inventor: Eugène N. M. Spronken, Genk, Belgium

[73] Assignee: Spronken Orthopedie, Belgium

[21] Appl. No.: 304,922

[22] Filed: Sep. 23, 1981

[30] Foreign Application Priority Data

Sep. 29, 1980 [BE] Belgium .................................. 885449

[51] Int. Cl.³ ............................ A43B 3/12; A43B 1/06
[52] U.S. Cl. ......................................... 36/11.5; 36/13; 36/86; 36/88; 36/110
[58] Field of Search .................... 36/13, 33, 85, 86, 87, 36/11.5, 110; 128/613

[56] References Cited

U.S. PATENT DOCUMENTS

| 1,406,033 | 2/1922 | Kingston | 36/13 |
| 2,526,205 | 10/1950 | Doerschler | 36/11.5 |
| 3,584,402 | 6/1971 | Silverman | 36/11.5 |
| 3,802,424 | 4/1974 | Newell | 128/82 |
| 3,859,727 | 1/1975 | Nakamoto | 36/11.5 |
| 3,916,538 | 11/1975 | Loseff | 36/11.5 |
| 4,206,558 | 6/1980 | Bivona | 36/11.5 |
| 4,309,832 | 1/1982 | Hunt | 36/33 |
| 4,314,412 | 2/1982 | Anderson et al. | 36/33 |
| 4,370,818 | 2/1983 | Simoglou | 36/110 |

FOREIGN PATENT DOCUMENTS

| 2712675 | 9/1978 | Fed. Rep. of Germany | 36/86 |
| 3036263 | 4/1981 | Fed. Rep. of Germany | 36/86 |

Primary Examiner—Louis Rimrodt
Assistant Examiner—Steven N. Meyers
Attorney, Agent, or Firm—Mason, Kolehmainen, Rathburn & Wyss

[57] ABSTRACT

A walking sole to be used under an immobilizing bandage on the lower leg whereby all foot joints are rigid, includes a running surface having three essentially flat parts which are spaced longitudinally and merge into one another with rounded transitions. A forward or toe part is curved upwards from a flat central part at an angle ranging between 25° and 35°. A hindmost or rear heel part slopes upwardly from the central part at an angle ranging between 15° and 25°. The vertical distance between the bottom of the central part and the highest point of the forward part is $(11\pm1)\%$ of a length factor, which factor equals 1.5 times the length of the sole in mm—15 mm. The vertical distance between said bottom and the highest point of the heel part is $(3\pm1)\%$ of said length factor. The rear end of the walking sole is approximately at a right angle relative to the bottom of the central part and the uppermost point of the rear end and of the front end lie in a plane which is approximately parallel to the bottom of the central part.

12 Claims, 6 Drawing Figures

WALKING SOLE

The present invention relates to a walking sole to be used under an immobilizing bandage of the lower leg whereby all foot joints are rigid.

The walking sole of the invention includes a running surface for contact with the ground which is curved upwards from a flat central part to a forward or toe part, positioned under the toes, and includes a rear heel part sloping upwardly from the central part positioned under the heel.

DESCRIPTION OF THE PRIOR ART

A walking sole is known from German patent application No. 2,712,675 having an upper surface, on which a bandage comes to rest, which is essentially flat. The running surface of the sole is curved over the entire length, but is curved only a little from the central part towards the back, with respect to the upper surface thereof. At the rear end of the sole, behind the heel of the wearer, an upright end surface is provided which extends upwardly approximately at a right angle to the upper surface of the sole.

With this known walking sole, the radius of curvature of the running surface is an average of the lengths or distances between the foot and the knee or the hip. The running surface is provided further with an elastic layer, designed to permit a rolling movement of the foot when walking.

It has appeared, however, that the natural movement of the foot is not circular at all and moreover, that the path of movement is dependent on the length of the foot. Thus, a certain instability occurs in the use of the known walking sole of said German patent application.

Furthermore, when the walking sole of said German patent application is used, the running surface will be placed on the ground with its rear edge first when the leg concerned is moved forwards. This develops a poor first contact with the ground which results in instability, and tends to cause angular rotations between the foot and the leg. This type of action is also the case with a still frequently used walking heel of the type having only a heel that is fixed or moulded to the immobilizing bandage and where the bandage itself in fact forms the heel.

From German patent application No. 2,827,410 it is known to provide a walking sole with a continuously curved running surface, which surface merges both at the front end and at the rear end under a sharp angle into the upper surface of the walking sole. The mergers are such, that the tangent lines on the running surface at said points include a certain angle with the upper surface of the walking sole.

A drawback of such a walking sole is that as a result of the continuous curve of the running surface, a stable support of the foot is never obtained in any position of the walking sole. As appears in particular from FIG. 1 of said German patent application, the walking sole does not extend over the entire length of the bandage, so that the bandage is not supported over its entire lower surface and in particular the forward part of the bandage can come into touch with the ground.

OBJECTS OF THE INVENTION

It is the purpose of the present invention to overcome the foregoing drawbacks by providing a walking sole, having a running surface shaped in such a way, that the natural movement of a human's walking process is approached as accurately as possible.

BRIEF SUMMARY OF THE INVENTION

According to the invention, the aforementioned drawbacks are overcome with a walking sole have a running surface, as seen in a longitudinal direction, which consists of three essentially flat parts. These flat parts merge into one another with rounded transitions, from a flat central or middle part to a forward or toe part which is curved upwardly at an angle $\beta$ between 25° and 35°. A hindmost or rear heel part slopes upwardly of the central part at an angle $\alpha$ between 15° and 25°. A vertical distance "d" between the bottom plane of the central part and the highest point of the toe part is dimensioned to be $(11\pm1)\%$ of a length factor "FL", which length factor "FL" equals 1.5 times the overall length "a" of the sole in mm.—15 mm. A vertical distance "e" between the bottom plane of the central part and the highest point of the heel part is dimensioned to be $(3\pm1)\%$ of the length factor "FL". A rear end of the walking sole forms approximately a right angle relative to the central bottom plane and the uppermost points of the rear end and the front end lie in a common plane, which is approximately parallel to the bottom of the flat central part.

The walking sole has a rear end portion at the heel with a much greater thickness than the thickness at the front end portion because the distance "e" is considerably smaller than the distance "d", whereas the upper level of the sole at both the front and back are positioned at approximately the same height above the central bottom plane.

The walking sole according to the invention extends from an upper edge of the rear end almost vertically downwards to intersect an inclined rear running surface 2 which forms an angle of about 20° with a bottom horizontal surface 3. The rear inclined surface 2 transitions in a curved radius 5 to merge into the flat central part 3. The flat central part 3 transitions through a rounded or curved portion 6 and merges into the forward or toe part 4, which slopes upwardly at an angle of 30° with respect to the horizontal plane of the central part.

According to a preferable embodiment of the invention, the flat central part 3 of the walking sole extends between a forward point defined at a distance "b" equal to $(38\pm3)\%$ of the factor "FL"$-(4\pm1)$ mm from the front end point of the walking sole and a rear point defined at a distance "f" equal to $(10\pm1)\%$ of the factor "FL"$+(4+1)$ mm from the rear end point of the walking sole. The distance "f" comprises the distance between the rear end point of the walking sole and the forward supporting point of the heel, and the line 8 at the distance "f" represents a transition point between leaning on the heel and leaning on the entire foot. The pivotal movement of the sole when the entire foot is put down, is around this transition point or line 8. The distance "b" is determined by the position of the middle foot bone of the big toe.

It is preferred that the inclined rear or heel flat part 2 of the walking sole extends from a point on a line 9 at a distance "h" equal to $(9\pm2)\%$ of the length factor "FL"$+(4\pm1)$ mm to the rear end point of the walking sole.

Between the point on line 9 and the earlier-mentioned point at the distance "f" on line 8, where the flat cenral part 3 begins, a parabolic transition 5 has been provided.

Of course, such a transition will always be present, although the tolerances of the distances "h" and "f" are such that the distances could become equal.

According to a further elaboration of the invention, a line 10 between the central part 3 of the walking sole 1 and the a rounded transition 6 towards the forward, upwardly inclined toe part 4, runs from a point on the inside edge "IE" of the sole, namely the side which is facing towards the user's other foot when the walking sole is used to the outside edge "OE". The point of beginning lies at a distance "b" from the front end point of the walking sole and forms an angle with a line 17 which is at a right angle to the longitudinal axis 7 of the walking sole. The angle is approximately 15° at the most and the line 10 extends rewardly from said beginning point on the inside edge "IE" of the sole as shown in FIG. 4.

From the line 10 at the distance "b", the central part 3 merges with a rounded transition 6 into the forward, upwardly inclined toe part 4. The rounded transition 6 terminates in a line 11 at a distance "k" from the front end point of the walking sole. The lines 10 and 11 are parallel and the distance "k" is (11+2)% of the length factor "FL".

BRIEF DESCRIPTION OF THE DRAWINGS

The invention will now be explained further by means of an example of an embodiment shown in the drawing, in which.

BRIEF DESCRIPTION OF THE PREFERRED EMBODIMENT

Figure 1:
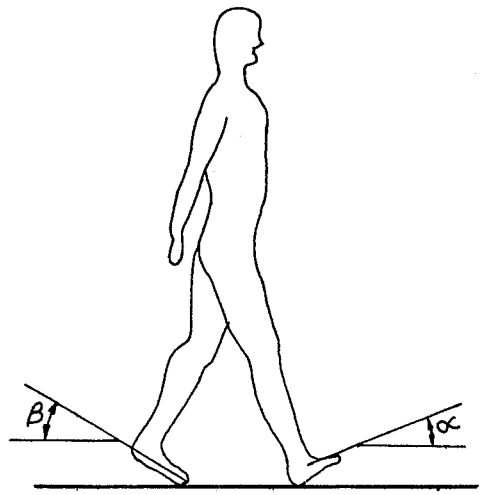
FIG. 1 schematically shows a side view of a walking person in order to show the angles which play a role in walking.

As appears in particular from FIG. 1, when a person walks, each leg moves forward and forms an angle $\alpha$ with respect to a perpendicular line, drawn from the hip joint. If the foot has been fixed at an angle of 90° with respect to the lower leg by means of an immobilizing bandage, the foot will touch the ground at an angle $\alpha$, of approximately 20°±5°.

Figure 2:
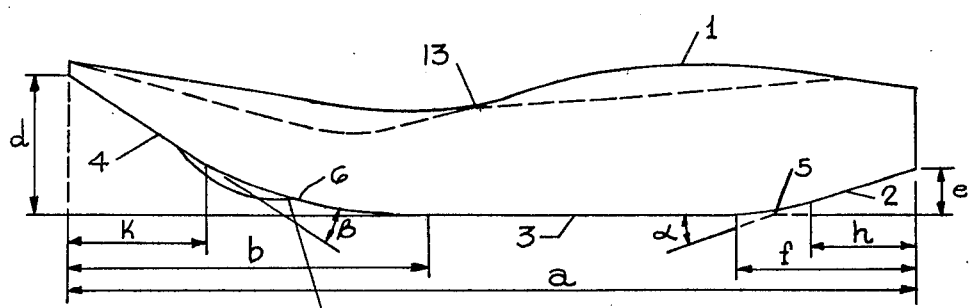
FIG. 2 schematically shows a side view of the walking sole according to the invention.

In connection therewith, the rear inclined surface 2 of the walking sole 1 shown in FIG. 2, forms an angle $\alpha$ with the horizontal plane, so that when the forwardly extended leg is put down, the surface 2 has a large area of contact surface with the ground.

The inclined surface 2 begins at a height "e" which equals (3±1)% of a length factor "FL". The term "FL" refers to a length factor or "fictive length", which equals 1.5 times (real length "a" in mm—15 mm).

The inclined part 2 merges with a rounded transition 5 into a flat central part 3. The flat central part 3 begins at a distance "f" from the rear end of the walking sole, and the distance "f" equals (10±1)% of the length factor "FL"+(4±1) mm. The flat central part 3 extends forwardly until reaching a distance "b" from the front end point of the walking sole, and the distance "b" equals (38±3)% of the length factor "FL"−(4±1) mm. The forward end point of the flat central part 3 merges into an upwardly inclined flat surface 4, which forms an angle $\beta$ with the horizontal plane, and the angle $\beta$ is 30°±5°.

The heel running surface 2 merges into the flat central part 3 via the parabolic transition 5, which begins at the distance "h" from the rear end of the walking sole. The distance "h" equals (9±2)% of the length factor "FL"+(4±1) mm.

With the above-mentioned lengths "b", "f" and "h", the length (4±1) mm corresponds to the thickness of the immobilizing bandage.

As said above, the user of the walking sole, when the leg concerned is put forward, will lean first on the flat heel part 2 and then through the transition 5 onto the flat central part 3. The user then leans on the whole foot and stands in a stable way, so that he can put the other leg forward without any problem. As soon as this leg leans sufficiently on the ground, the foot provided with the walking sole will swivel with respect to the ground, until the walking sole takes the position in which the front or toe surface 4 leans almost entirely on the ground. The highest point of the surface 4 is at a distance "d" above the horizontal plane, and the distance "d" equals (11±1)% of the length factor "FL". At this moment the wearer's leg has taken the position as shown in FIG. 1 for the hindmost leg.

The front or toe surface 4 merges through rounded transition 6 into the flat central part 3. The rounded transition 6 begins at a distance "k" from the front end of the walking sole, and the distance "k" equals (11±2)% of the length factor "FL".

Figure 4:
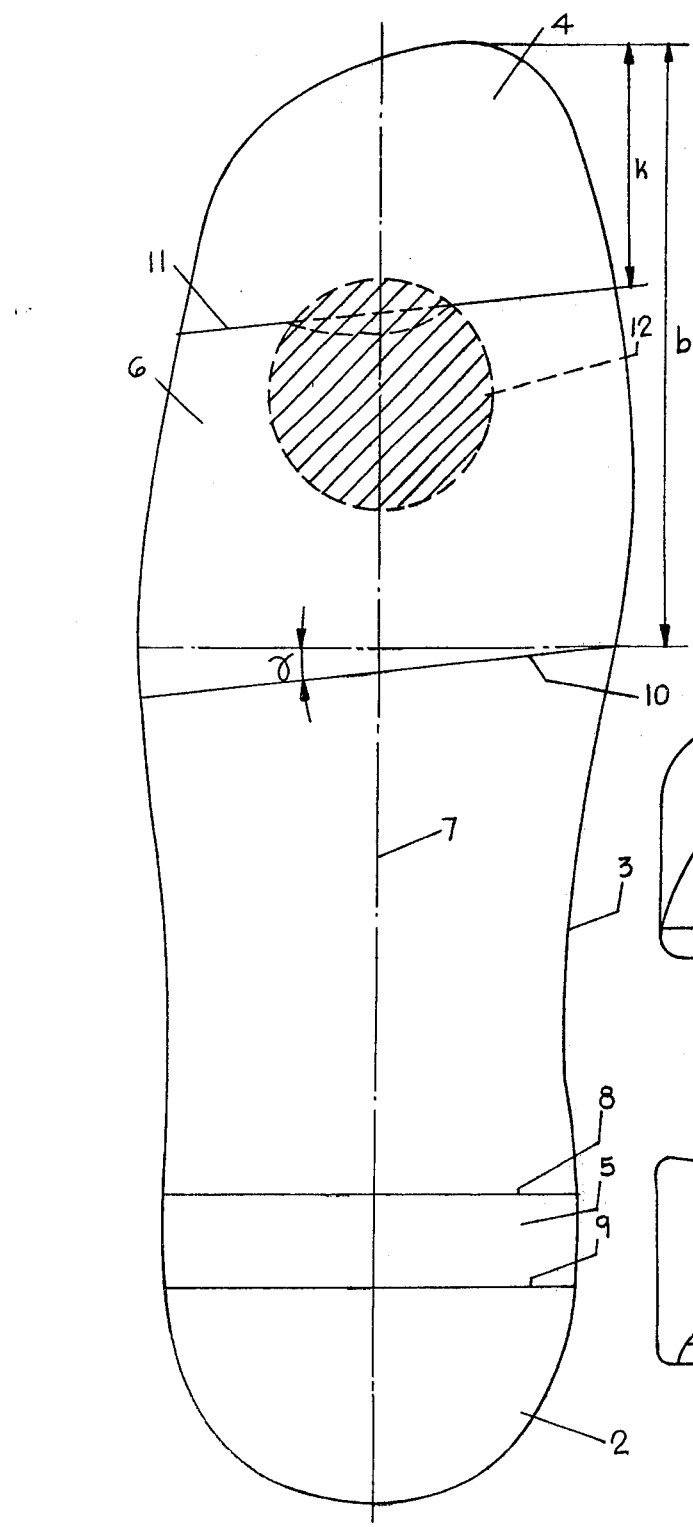
FIGS. 4, 5 and 6 respectively show a bottom view, a front view and a rear view of the walking sole according to FIG. 2.
Figure 5:
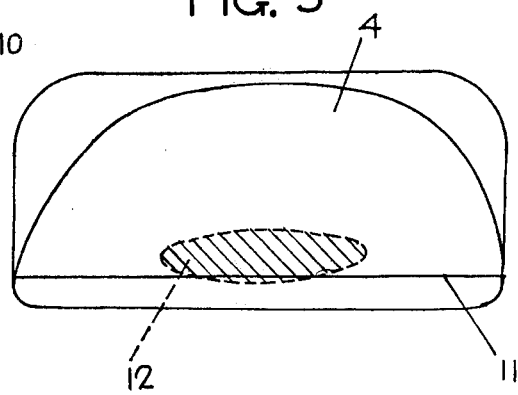
Figure 6:
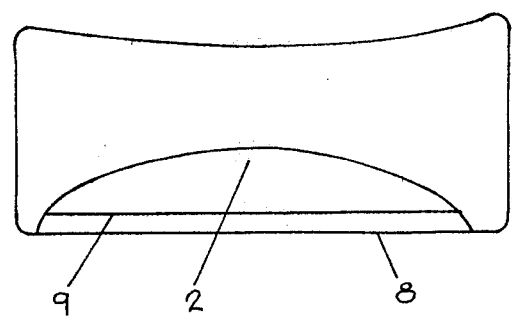

FIG. 4 shows a bottom view of the walking sole of FIG. 2. The longitudinal direction or axis of the walking sole 1 is indicated by the line 7. The transition lines 8 and 9 between the parts 2 and 3 are at a right angle to the line 7, but the transition lines 10 and 11 between the parts 3 and 4 form an angle $\gamma$ with respect to a dotted line 17, which is at a right angle to the axis line 7. The angle $\gamma$ equals 10°±5° and is directed in such a way, that the lines 10 and 11 are slanted to the outside edge of the walking sole towards the lines 8 and 9. Thus the foot will make a slightly outwardly directed movement, as is also the case in normal walking.

As said above and as appears from FIG. 4, the line 10 begins at a point of the inside edge of the walking sole which lies at a distance "b" from the front end point. The line 11 begins at a point on the walking sole spaced at a distance "k" from the front end.

In order to facilitate the turning of the foot, a small shallow sloped convex protrusion 12, outlined by a circle, may be provided in the toe part 4 and partly in the front transition area 6. The protrusion 12 gradually merges at all sides into the adjacent running surface of the walking sole.

As appears from FIG. 2, the front end point of the upper surface 13 of the walking sole 1 lies approximately at the same height as the hindmost point thereof and the shape of the upper surface 13 has been adapted to the shape of the foot, so that, if the immobilizing bandage is applied over the entire foot in approximately the same thickness, good support of the bandage and therefore of the foot is obtained.

For an optimal support it will be desirable to manufacture the walking sole in different sizes and also separate soles for the left and the right foot. A walking sole of a rigid material will be desired, as otherwise the effect of the specific shape of the lower surface will be lost.

Figure 3:
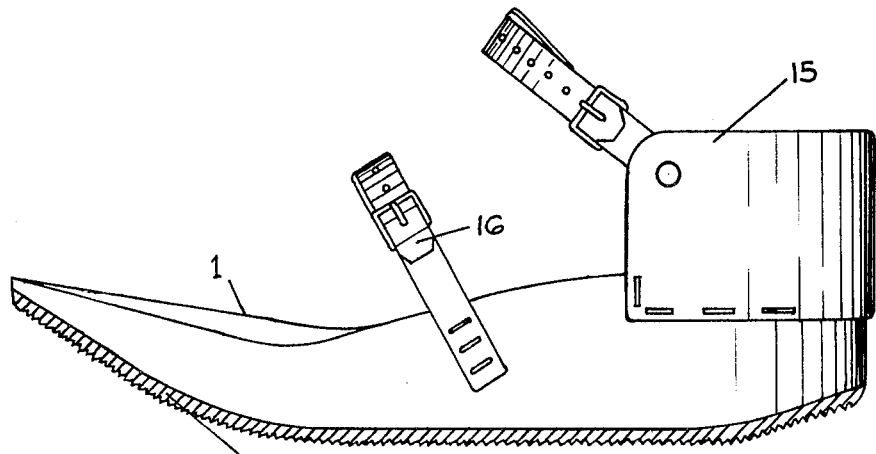
FIG. 3 shows a side view of the walking sole provided with additional parts adapted for securing the walking sole to the foot.

Thus for example, an embodiment of the sole 1 in wood is possible, with which it may be desirable to provide a lower surface with a thin layer of rubber 14 or a similar material, as shown in FIG. 3, in order to obtain some shock absorption when the foot is put down and also to make the lower surface sufficiently non-slip, so that slipping is avoided. FIG. 3 also shows how the walking sole can be provided with an ankle piece 15 and a froint strap 16 to secure the walking sole firmly on the foot.

Although the present invention has been described with reference to an illustrated embodiment thereof, it should be understood that numerous other modifications and embodiments can be made by those skilled in the art that will fall within the spirit and scope of the principles of this invention.

What is claimed as new and desired to be secured by Letters Patent is:

1. A walking sole adapted to be used under an immobilizing bandage on the lower leg for maintaining all foot joints in a rigid condition, said walking sole having a lower running surface coming into contact with the ground formed of three longitudinally spaced essentially flat parts, and said flat parts joining one another with rounded transitions, a forward one of said parts curved upwardly from a central part at an angle betwen 25° and 35° and a rear heel part sloping upwardly of said central part at an angle between 12° and 25°, sole dimensioned to provide a distance between a bottom plane of said central part to a highest point of said forward part of $(11\pm1)\%$ of a length factor and having a distance between said bottom plane of said central part and a highest point of said rear part of $(3\pm1)\%$ of said length factor, said length factor equal to 1.5 times the length of said sole in mm—15 mm, a rear end of said walking sole aligned approximately at a right angle to said central bottom plane, and an uppermost point of said rear end and an uppermost point on a front end of said sole aligned to lie in a plane approximately parallel to said bottom central plane.

2. A walking sole according to claim 1, wherein said flat central part of said sole is dimensioned to extend between a forward point spaced a distance equal to $(38\pm3)\%$ of said length factor less $(4\pm1)$ mm from a foremost point of said walking sole and a rearward point spaced at the distance equal to $(10\pm1)\%$ of said length factor plus $(4\pm1)$ mm from a rearmost point of the walking sole.

3. A walking sole according to claim 1, in which said inclined, flat rear heel part of said walking sole is dimensioned to extend rearwardly of a point spaced at a distance equal to $(9\pm2)\%$ of said length length plus $(4\pm1)$ mm from a rearmost point of the walking sole.

4. A walking sole according to claim 1, in which a curved parabolic transition is provided between said flat rear heel part and said flat central part.

5. A walking sole according to claim 2, wherein said flat central part of said walking sole is merged into a forward rounded transition part at a forward end to join said forward, upwardly inclined part, said transition starting at a transition line beginning at a point on the inside edge of said sole at said indicated distance from said foremost point of said walking sole and making an angle with a line at a right angle to a longitudinal axis of said walking sole, of not more than 15° and extending rearwardly from said starting point on the inside edge of the sole.

6. A walking sole according to claim 5, wherein said forward rounded transition part merges into said forward upwardly inclined toe part along a second transition line parallel of said first mentioned transition line, said second transition line starting a point on the inside edges of said walking sole which lies at a distance from the foremost point of the walking sole equalling $(11\pm2)\%$ of said length factor.

7. A walking sole according to claim 1, including a small convex circular protrusion formed on said forward upwardly inclined toe part and said forward transition part.

8. A walking sole according to claim 1, having an upper surface shaped to match the sole of a foot.

9. A walking sole according to claim 1, having a length determined by the length of an intended user's foot.

10. A walking sole according to claim 1 made of a rigid material.

11. A walking sole according to claim 10, including a thin layer of non-skid, resilient material on said running surface.

12. A walking sole according to claim 1 including angle holding means and a strap forward thereof for securing said walking sole on the foot of a user.

* * * * *